US011559539B2

(12) United States Patent
Potappel-Van 'T Land et al.

(10) Patent No.: US 11,559,539 B2
(45) Date of Patent: Jan. 24, 2023

(54) HUMAN MILK OLIGOSACCHARIDE FOR IMPROVING IMMUNE FITNESS

(71) Applicant: N.V. Nutricia, Zoetermeer (NL)

(72) Inventors: Belinda Potappel-Van 'T Land, Utrecht (NL); Lieke Wilhelmina Johanna Van Den Elsen, Best (NL); Bernd Stahl, Ultrecht (NL)

(73) Assignee: N.V. Nutricia, Zoetermeer (NL)

( * ) Notice: Subject to any disclaimer, the term of this patent is extended or adjusted under 35 U.S.C. 154(b) by 25 days.

(21) Appl. No.: 16/785,712

(22) Filed: Feb. 10, 2020

(65) Prior Publication Data

US 2020/0171062 A1  Jun. 4, 2020

Related U.S. Application Data

(63) Continuation of application No. PCT/NL2018/050481, filed on Jul. 12, 2018.

(30) Foreign Application Priority Data

Aug. 11, 2017 (WO) ............... PCT/NL2017/050532

(51) Int. Cl.
A61K 31/702 (2006.01)
A23L 33/00 (2016.01)

(52) U.S. Cl.
CPC ............ *A61K 31/702* (2013.01); *A23L 33/40* (2016.08)

(58) Field of Classification Search
CPC .................................................. A61K 31/702
See application file for complete search history.

(56) References Cited

U.S. PATENT DOCUMENTS

| | | | |
|---|---|---|---|
| 5,002,759 A | 3/1991 | Gaffar et al. | |
| 6,576,251 B1 | 6/2003 | Stahl et al. | |
| 8,591,919 B2 | 11/2013 | Stahl | |
| 9,566,291 B2 | 2/2017 | Boehm et al. | |
| 10,420,784 B2 | 9/2019 | Stahl et al. | |
| 2002/0019991 A1 | 2/2002 | Prieto et al. | |
| 2007/0274983 A1 | 11/2007 | Kluijtmans et al. | |
| 2007/0275881 A1 | 11/2007 | Morrow et al. | |
| 2008/0124323 A1 | 5/2008 | Boehm et al. | |
| 2008/0145838 A1 | 6/2008 | Suda et al. | |
| 2009/0221486 A1 | 9/2009 | Schmitt et al. | |
| 2012/0177691 A1 | 7/2012 | Stahl et al. | |
| 2012/0178674 A1 | 7/2012 | Stahl et al. | |
| 2015/0031645 A1 | 1/2015 | Buck et al. | |
| 2016/0316808 A1 | 11/2016 | Destaillats et al. | |
| 2016/0354395 A1 | 12/2016 | Contractor et al. | |

FOREIGN PATENT DOCUMENTS

| | | |
|---|---|---|
| EP | 1 105 002 B1 | 6/2001 |
| EP | 1 105 002 B2 | 6/2001 |
| EP | 1 597 978 A1 | 11/2005 |
| EP | 1 629 850 A1 | 3/2006 |
| EP | 1 629 850 B2 | 3/2006 |
| EP | 1 629 850 B1 | 5/2007 |
| EP | 2 072 052 A1 | 6/2009 |
| EP | 2 662 084 | 11/2013 |
| EP | 2 813 230 | 12/2014 |
| WO | WO-99/11773 A1 | 3/1999 |
| WO | WO-99/56754 A1 | 11/1999 |
| WO | WO-00/08948 A2 | 2/2000 |
| WO | WO-01/64225 A1 | 9/2001 |
| WO | WO-2005/039319 A2 | 5/2005 |
| WO | WO-2005/039597 A2 | 5/2005 |
| WO | WO-2005/055944 A2 | 6/2005 |
| WO | WO-2007/010084 A2 | 1/2007 |
| WO | WO-2007/067053 A1 | 6/2007 |
| WO | WO-2007/105945 A2 | 9/2007 |
| WO | WO-2007/114683 A1 | 10/2007 |
| WO | WO-2009/065905 A2 | 5/2009 |
| WO | WO-2009/077352 A1 | 6/2009 |
| WO | WO-2011/008086 A1 | 1/2011 |
| WO | WO-2011/008087 A1 | 1/2011 |
| WO | WO-2015/071391 A1 | 5/2015 |

OTHER PUBLICATIONS

Goehring, K. C. et al., The Journal of Nutrition, "Similar to those who are breastfed, infants fed a formula containing 2'-fucosyllactose have lower inflammatory cytokines in a randmized controlled trial", 2016, vol. 146, pp. 2559-2566 (Year: 2016).*
Zivkovic, I. et al., Vaccine, "Sexual diergism in antibody response to whole virus trivalent inactivated influenza vaccine in outbred mice", 2015, vol. 33, pp. 5546-5552. (Year: 2015).*
Sela, D. et al., Trends in Microbiology, "Nursing our microbiota: molecular linkages between bifidobacteria and milk oligosaccharides", 2010, vol. 7, pp. 298-307 (Year: 2010).*
Jansen, A. et al., J. Pediatr., "Effects of Influenza Plus Pneumococcal Conjugate Vaccination Versus Influenza Vaccination Alone in Preventing Respiratory Tract Infections in Children: A Randomized, Double-Blind, Placebo-Controlled Trial", 2008, vol. 153, pp. 764-770 (Year: 2008).*
Block, Stan, The Pediatric Infectious Disease Journal, "New Data on Influenza Vaccines in Children", 2004, vol. 23, No. 1, p. 85 (Year: 2004).*
Van de Witte, S.V. et al., Trials in Vaccinology, "Trivalent inactivated subunit influenza vaccine Influvac(R): 30-year experience of safety and immunogenicity", 2012, vol. 1, pp. 42-48 (Year: 2012).*
Zangwill, K. et al., Pediatric Infectious Disease Journal, "Safety and efficacy of trivalent inactivated influenza vaccine in young children: a summary for the new era of routine vaccination" 2004, vol. 23, pp. 189-200 (Year: 2004).*
"Annex E: In vitro lactate production upon fermentation of different ratio's of galacto-oligosaccharides and inulin by infant's faeces", Appeal proceedings of EP1105002 (E17b), filed with letter of patentee on Dec. 3, 2008 (2 pages).
"Bioprocesses and Biotechnology for Functional Foods and Nutraceuticals", Edited by Jean-Richard Neeser and J. Bruce German, 2004, pp. 103-105 (5 pages).

(Continued)

*Primary Examiner* — Bahar Craigo
(74) *Attorney, Agent, or Firm* — N.V. Nederlandsch Octrooibureau

(57) ABSTRACT

The invention concerns the use of fucosylated non-digestible human milk oligosaccharide, or a composition comprising a fucosylated non-digestible human milk oligosaccharide, for use in improving immune fitness in a human subject, wherein the human subject is male.

2 Claims, No Drawings

(56) References Cited

OTHER PUBLICATIONS

"Childhood Vaccine Schedule", NIH Medline Plus, Spring 2008, retrieved Apr. 10, 2013 from URL: http://www.nlm.nih.gov/medlineplus/magazine/issues/spring08/articles/spring08pg7.html (2 page).

"Dog Vaccination Schedule", Dog Care: Vaccination Schedule, Nov. 29, 2008, retrieved Apr. 10, 2013 from URL: http://samanjith.blogspot.com/2008/11/dog-vaccination-schedule.html (5 pages).

"Milk Facts: Nutritional Components in Milk", MilkFacts.info, retrieved Oct. 23, 2012 from URL: http://www.milkfacts.info/Nutrition%20Facts/Nutritional%20Components.htm (7 pages).

"Prebiotics in Infant Nutrition", edited by Sharon Donovan, Glenn Gibson, and David Newburg, Mead Johnson Nutrition, 2009, pp. 1-37 (21 pages).

"The Condensed Chemical Dictionary", revised by Gessner G. Hawley, 10th ed., 1981, pp. 759 (3 pages).

Acknowledgement of Receipt and Letter in reply to communication under Rule 161(1) EPC in European Application No. 10734842.7 dated Sep. 10, 2012 (4 pages).

Benyacoub et al., "Feeding a Diet Containing a Fructooligosaccharide Mix Can Enhance *Salmonella* Vaccine Efficacy in Mice", Journal of Nutrition, Nutritional Immunology, American Society for Nutrition, vol. 138, 2008, pp. 123-129 (7 pages).

Bode, Lars, "Recent Advances on Structure, Metabolism, and Function of Human Milk Oligosaccharides", The Journal of Nutrition: Recent Advances in Nutritional Sciences, 2006, vol. 136, pp. 2127-2130 (4 pages).

Carver, Jane D, "Advances in nutritional modifications of infant formulas", The American Journal of Clinical Nutrition, 2003, vol. 77(suppl), pp. 1550S-1554S (5 pages).

Charlwood et al., "A detailed analysis of Neutral and Acidic Carbohydrates in Human Milk", Analytical Biochemistry, 1999, vol. 273, pp. 261-277 (17 pages).

Claud et al., "Hypothesis: inappropriate colonization of the premature intestine can cause neonatal necrotizing enterocolitis", The FASEB Journal, Jun. 2001, vol. 15, No. 8, pp. 1398-1403 (6 pages).

Crittenden et al., "Production, properties and applications of food-grade oligosaccharides", Trends in Food Science & Technology, Nov. 1996, vol. 71, pp. 353-361 (9 pages).

ENVIRON International Corporation, "Generally Recognized as Safe (GRAS) Determination for the Use of Galacto-Oligosaccharides (GOS) in Foods and Term Infant Formulas", Vivinal (R), pp. I-iii, 1-4, Sep. 6, 2007 (8 pages).

ENVIRON International Corporation, "GRAS Exemption Claim for Galacto-Gligosaccharides(GOS)" Friesland Foods Domo, Oct. 18, 2007, pp. 1-4 (9 pages).

Faldella et al., "The preterm infant's antibody response to a combined diphtheria, tetanus, acellular pertussis and hepatitis B vaccine", Vaccine, 1998, vol. 16, No. 17, pp. 1646-1649 (4 pages).

Fanaro et al., "Galacto-oligosaccharides and long-chain fructo-oligosaccharides as prebiotics in infant formulas: A review", Acta Pediatrica, 2005, vol. 94 (Suppl 449), pp. 22-26 (6 pages).

Final Office Action for U.S. Appl. No. 13/383,823 dated May 25, 2016 (10 pages).

Grollman et al. "Biosynthesis of Fucosyllactose and Other Oligosaccharides Found in Milk*", The Journal of Biological Chemistry, vol. 240, No. 3, Mar. 1965 (7 pages).

Haug et al., "Bovine milk in human nutrition—a review", Lipids in Health and Disease, vol. 6, No. 25, pp. 1-16, Sep. 25, 2007 (16 pages).

Hesseling et al., "Consensus statement on the revised World Health Organization recommendations for BCG vaccination in HIV-infected infants", Int J Tuberc Lung Dis, 2008, vol. 12, No. 12, pp. 1376-1379 (4 pages).

Interlocutory decision in oppositions proceedings (Art. 101(3)(a) and 106(2) EPC) issued in European Application No. 04 077 394.7 dated Jul. 20, 2012 (21 pages).

International Preliminary Report on Patentability, Ch. I, for PCT/NL2010/050446 dated Jan. 17, 2012 (7 pages).

International Preliminary Report on Patentability, Ch. II, for PCT/NL2010/050447 dated Oct. 19, 2011 (13 pages).

International Search Report and Written Opinion of the International Searching Authority for PCT/NL2018/050481 dated Dec. 4, 2018 (14 pages).

International Search Report for PCT/NL2010/050446 dated Oct. 19, 2010 (5 pages).

International Search Report for PCT/NL2010/050447 dated Oct. 19, 2010 (5 pages).

Kidd, Parris, "Th1/Th2 Balance: The Hypothesis, its Limitations, and Implications for Health and Disease", Alternative Medicine Review, 2003, vol. 8, No. 3, pp. 223-246 (24 pages).

Kohlhuber et al., "Breastfeeding rates and duration in Germany: a Bavarian cohort study", British Journal of Nutrition, May 2008, vol. 99, No. 5, pp. 1127-1132, (6 pages).

Kovarik et al., "Optimization of vaccine responses in early life: The role of delivery systems and immunomodulators", Immunology and Cell Biology, 1998, vol. 76, pp. 222-236 (15 pages).

Krathwohl et al., "Chemokine CXCL 10 (IP-10) is sufficient to trigger an immune response to injected antigens in a mouse model," Vaccine, vol. 24, 2006 pp. 2987-2993 (7 pages).

Minna-Maija et al., "Fecal Microflora in Healthy Infants Born by Different Methods of Delivery: Permanent Changes in Intestinal Flora after Cesarean Delivery", Journal of Pediatric Gastroenterology & Nutrition, Jan. 1999, vol. 28, No. 1, pp. 19-25 (13 pages).

Mitoulas et al., "Variation in fat, lactose and protein in human milk over 24h and througout the first year of lactation", British Journal of Nutrition, 2002, vol. 88, pp. 29-37 (9 pages).

Morrow et al., "Human-Milk Glycans That Inhibit Pathogen Binding Protect Breast-Feeding Infants against Infectious Diarrhea", The Journal of Nutrition, American Society for Nutritional Sciences, 2005, vol. 135, No. 5, pp. 1304-1307 (4 pages).

Nakamura et al. "The Milk Oligosaccharides of Domestic Farm Animals", Trends in Glycoscience and Glycotechnology, Mar. 2004, vol. 16, No. 88, pp. 135-142 (8 pages).

Newburg et al., "Innate protection conferred by fucosylated oligosaccharides of human milk against diarrhea in breastfed infants", Glycobiology, 2004, vol. 14, No. 3, pp. 253-263 (11 pages).

Newburg et al., "Neonatal protection by an innate immune system of human milk consisting of oligosaccharides and glycans", Journal of Animal Science, 2009, vol. 87, pp. 26-34 (11 pages).

Ninonuevo et al., "Infant Formula Oligosaccharides Opening the Gates (for Speculation)", Pediatric Research, 2008, vol. 64, No. 1, pp. 8-10 (3 pages).

Nittynen et al., "Galacto-oligosaccharides and bowel function", Scandinavian Journal of Food and Nutrition, 2007, vol. 51, No. 2, pp. 62-66 (5 pages).

Non-Final Office Action for U.S. Appl. No. 13/383,823 dated Oct. 7, 2015 (10 pages).

Oftedal, Olav T., "Lactation in the Dog: Milk Composition and Intake by Puppies", The Journal of Nutrition, vol. 114, 1984, pp. 803-812 (10 pages).

Ruiz-Palacios et al., "Campylobacter jejuni Binds Intestinal H(O) Antigen (Fucal, 2GalB1, 4GlcNAc), and Fucosyloligosaccharides of Human Milk Inhibit Its Binding and Infection*", The Journal of Biological Chemistry, Apr. 18, 2003, vol. 278, No. 16, pp. 14112-14120 (9 pages).

Sotgiu et al., "Immunomodulation of fucosyl-lactose and lacto-N-fucopentaose on mononuclear cells from multiple sclerosis and healthy subjects", International Journal of Biomedical Science, vol. 2, No. 2, Jun. 15, 2006, pp. 114-120 (7 pages).

Sumiyoshi et al., "Determination of each neutral oligosaccharide in the milk of Japanese women during the course of lactation", British Journal of Nutrition, Jan. 2003, vol. 89, No. 1, pp. 61-69 (9 pages).

Torres et al., "Galacto-Oligosaccharides: Production, Properties, Applications, and Significance as Prebiotics", Comprehensive Reviews in Food Science and Food Safety, 2010, vol. 9, pp. 438-454 (17 pages).

(56) References Cited

OTHER PUBLICATIONS

Urashima et al., "Chemical characterization of oligosaccharides in chimpanzee, bonobo, gorilla, orangutan, and siamang milk or colostrum", Glycobiology, vol. 19, No. 5, 2009, pp. 499-508 (10 pages).
Urashima et al., "Oligosaccharides of milk and colostrum in non-human mammals", Glycoconjugate Journal, 2001, vol. 18, pp. 357-371 (15 pages).
Vandenplas, Y., "Oligosaccharides in Infant Formula", British Journal of Nutrition, 2002, vol. 87, Suppl. 2, pp. S293-S296 (4 pages).
Vos et al., "A specific prebiotic oligosaccharide mixture stimulates delayed-type hypersensitivity in a murine influenza vaccination model", International Immunopharmacology, 2006, vol. 6, pp. 1277-1286 (10 pages).
Vos et al., "Dietary supplementation of neutral and acidic oligosaccharides enhances Th1-dependent vaccination responses in mice", Pediatric Allergy and Immunology, 2007, vol. 18, pp. 304-312 (9 pages).
Zoppi et al., "Diet and Antibody Response to Vaccinations in Health Infants", The Lancet, Jul. 2, 1983, pp. 11-14 (4 pages).

\* cited by examiner

HUMAN MILK OLIGOSACCHARIDE FOR IMPROVING IMMUNE FITNESS

CROSS-REFERENCE TO RELATED APPLICATIONS

This application is a continuation of International Application No. PCT/NL2018/050481, filed Jul. 12, 2018, which claims the benefit of and priority to International Application No. PCT/NL2017/050532, filed Aug. 11, 2017, both of which are hereby incorporated by reference herein in their entireties.

FIELD OF THE INVENTION

The present invention is in the field of infant nutrition involving specific human milk oligosaccharides.

BACKGROUND OF THE INVENTION

Human milk is the preferred food for infants and is also denoted as the golden standard. One of the reasons for this is the relatively high inclusion level of human milk oligosaccharides (HMOs) which are non-digestible oligosaccharides (NDOs). These HMOS form a complex mixture of prebiotic molecules that form an excellent substrate for beneficial microbiota to thrive on. HMOs, being part of mother's milk, are of course mostly relevant to help infants build the beneficial microbiota needed for optimal health.

It is known that the state of the intestinal microbiota is directly linked to one's health. The intestinal microbiota consists of a large association of beneficial bacteria which is believed to be unique for each individual, but which fulfils the same overall physiological functions. These functions include preventing other pathogenic microorganisms from proliferating, ensuring a proper digestive functioning and ensuring a proper intestinal barrier which is important for the immune system to function.

Methods for selectively stimulating the beneficial microbiota include administering live beneficial bacteria (usually denoted as probiotics) to a human subject and administering a substrate for beneficial microbiota to grow on (usually called prebiotics) to a human subject.

The most abundant HMO in human milk is 2'-fucosyllactose (2'-FL). For this oligosaccharide it is known that it can boost the immune system and prevent against infection. For instance, from WO 2015/071391 it is known that 2'-fucosyllactose is beneficial for the prevention and treatment of viral influenza.

SUMMARY OF THE INVENTION

It has now surprisingly been found that the administration of human milk oligosaccharides has an unexpected effect in male subjects on enhancing the vaccination response. More specifically the inventors have found that administering a composition comprising a fucosylated non-digestible human milk oligosaccharide, in particular comprising 2'-fucosyllactose, gives a boost to the vaccination response in male subjects, wherein the male subjects are preferably infants.

This has been experimentally established by vaccinating males and females with a trivalent influenza vaccine and measuring the Ig-G levels after said vaccination. Surprisingly the control group showed that females respond much better to the vaccination than males do. Even more surprising it was shown that it is possible to repair the low vaccination response in the males by administering a composition comprising 2'-fucosyllactose and preferably comprising further non digestible oligosaccharides.

A beneficial effect on enhancing immune response is closely related to the subjects' overall immune fitness. This concept of immune fitness refers to the health of the immune system or the ability of the immune system to neutralize a harmful pathogen. An immune system that is fit has the ability to respond quickly and adequately to a potentially harmful pathogen.

A closely related to immune fitness is immune balance. A healthy immune system is neither overactive nor underactive. Instead it is balanced between these two extremes. Hence a healthy immune system necessarily is a balanced immune system.

DETAILED DESCRIPTION OF THE INVENTION

The present invention thus concerns a method for improving immune fitness, restoration of immune balance and/or enhancing vaccine specific immune response in a human subject, comprising administering a fucosylated non-digestible human milk oligosaccharide, or a composition comprising a fucosylated non-digestible human milk oligosaccharide, to the human subject, wherein the human subject is male.

The invention may also be worded as the use of a fucosylated non-digestible human milk oligosaccharide, or a composition comprising a fucosylated non-digestible human milk oligosaccharide, for the manufacture of a composition for improving immune fitness, restoration of immune balance and/or enhancing vaccine specific immune response in a human subject, wherein the human subject is male.

In other words the invention relates to the use of a fucosylated non-digestible human milk oligosaccharide, or a composition comprising a fucosylated non-digestible human milk oligosaccharide, for improving immune fitness, restoration of immune balance and/or enhancing vaccine specific immune response in a male human subject.

For some jurisdictions, the invention may also be worded as a fucosylated non-digestible human milk oligosaccharide, or a composition comprising a fucosylated non-digestible human milk oligosaccharide, for use in improving immune fitness, restoration of immune balance and/or enhancing vaccine specific immune response in a human subject, wherein the human subjects is male.

In a particularly preferred embodiment, the present concerns enhancing vaccine specific immune response.

Hence, the present invention concerns a method for enhancing vaccine specific immune response in a human subject, comprising administering a fucosylated non-digestible human milk oligosaccharide, or a composition comprising a fucosylated non-digestible human milk oligosaccharide, to the human subject, wherein the human subject is male.

The invention may also be worded as the use of a fucosylated non-digestible human milk oligosaccharide, or a composition comprising a fucosylated non-digestible human milk oligosaccharide, for the manufacture of a composition for enhancing vaccine specific immune response in a human subject, wherein the human subject is male.

In other words the invention relates to the use of a fucosylated non-digestible human milk oligosaccharide, or a composition comprising a fucosylated non-digestible human milk oligosaccharide, for enhancing vaccine specific immune response in a male human subject.

For some jurisdictions, the invention may also be worded as a fucosylated non-digestible human milk oligosaccharide, or a composition comprising a fucosylated non-digestible human milk oligosaccharide, for use in enhancing vaccine specific immune response in a human subject, wherein the human subjects is male.

The vaccine specific immune response is preferably an antibody response and more preferably an IgG response. In a preferred embodiment, the vaccine specific immune response is an influenza vaccine response. In a further preferred embodiment, the influenza vaccine response is in response to a single vaccination. In a further preferred embodiment, the influenza vaccine response is in response to a vaccination with inactivated vaccine, or in other words to a vaccine of inactivated virus particles. Preferably the single vaccination is a single influenza vaccination and more preferably said vaccination is a single trivalent influenza vaccination. Preferably the single vaccination is a single influenza vaccination of inactivated virus particles, and more preferably said vaccination is a single trivalent influenza vaccination of inactivated trivalent virus particles.

In a preferred embodiment, the male human subject is a male infant in need of having an enhanced vaccine specific immune response. Most preferably, the vaccine specific immune response is an influenza vaccine response. In one embodiment the vaccine specific immune response is a trivalent influenza vaccine response.

In a preferred embodiment the fucosylated non-digestible human milk oligosaccharide is 2'-fucosyllactose (2'-FL). In an even more preferred embodiment the composition comprising a fucosylated non-digestible human milk oligosaccharide also comprises other non-digestible oligosaccharides such as galactooligosaccharides (GOS) and/or fructooligosaccharides (FOS). In a preferred embodiment the composition comprising a fucosylated non-digestible human milk oligosaccharide comprises 2'-FL and short chain GOS (scGOS). In a preferred embodiment the composition comprising a fucosylated non-digestible human milk oligosaccharide comprises 2'-FL and short chain GOS (scGOS) and long chain FOS (lcFOS).

NDOs

Prebiotics are typically indigestible sugar-type compounds such as non-digestible oligosaccharides (NDOs). These compounds pass through the first part of the gastrointestinal tract substantially without being digested. In the intestine these compounds are fermented by the microbiota releasing, amongst others, short chain fatty acids which are adsorbed by the human body.

There are many sources of NDO's, amongst which is human breast milk. Usually these oligosaccharides are denoted as human milk oligosaccharides (HMOs). Typical NDOs used in infant foods are GOS and FOS.

Human Milk Oligosaccharides

Human milk is the preferred food for infants and is also denoted as the golden standard. Human milk contains a particularly high level of oligosaccharides of roughly 10 g/L, which is typically much more than the level of NDO in the milk from domestic animals. Also, compared to the NDOs in the milk of domestic animals, HMOs are structurally different. Human NDOs are very complex and consist of a heterogenic group of more than 130 different compounds with a diverse sugar composition. Because of their complex and polymorphic structure, large-scale synthesis is compli- cated. It is therefore not yet technically and economically feasible to prepare compositions, such as infant formulas, with NDO composition identical to human milk. In the method or use according to the present, a fucosylated non-digestible human milk oligosaccharide is used.

Fucosylated Non-Digestible Human Milk Oligosaccharides

Fucosyllactose (FL) is a fucosylated non-digestible oligosaccharide present in human milk. It is not present in bovine milk. It consists of three monosaccharide units, fucose, galactose and glucose linked together. Lactose is a galactose unit linked to a glucose unit via a beta 1,4 linkage. A fucose unit is linked to a galactose unit of a lactose molecule via an alpha 1,2 linkage (2'-fucosyllactose, 2'-FL) or via an alpha 1,3 linkage to the glucose unit of a lactose (3-Fucosyllactose, 3-FL). 2'FL is the most abundant NDO in human milk. The HMO used in the current invention is most preferably 2'-FL.

2'-FL, (β-L-Fuc-(1→2)-β-D-Gal-(1→4)-D-Glc) and 3-FL (β-L-Fuc-(1→3)-[β-D-Gal-(1→4)]-D-Glc), are commercially available for instance from Sigma-Aldrich. Alternatively, they can be isolated from human milk, for example as described in Andersson & Donald, 1981, J Chromatogr. 211:170-1744, or produced by genetically modified microorganisms, for example as described in Albermann et al, 2001, Carbohydrate Res. 334:97-103.

Preferably, a composition according to the invention comprises 1 mg to 3 g fucosyllactose per 100 ml, more preferably 10 mg to 2 g, more preferably 20 mg to 200 mg, even more preferably 20 mg to 150 mg FL per 100 ml. Based on dry weight, the present composition preferably comprises 0.007 wt. % to 20 wt. % fucosyllactose, more preferably 0.07 wt. % to 10 wt. %, more preferably 0.15 wt. % to 5 wt. %, more preferably 0.15 wt. % to 2 wt. %, even more preferably 0.15 wt. % to 1 wt. %. Preferably, a composition according to the invention comprises 1 mg to 3 g 2'-FL per 100 ml, more preferably 10 mg to 2 g, more preferably 20 mg to 200 mg, even more preferably 20 mg to 150 mg 2'-FL per 100 ml. Based on dry weight, the present composition preferably comprises 0.007 wt. % to 20 wt. % 2'-FL, more preferably 0.07 wt. % to 10 wt. %, more preferably 0.15 wt. % to 5 wt. %, more preferably 0.15 wt. % to 2 wt. %, even more preferably 0.15 wt. % to 1 wt. %. A lower amount of fucosyllactose will be less effective in stimulating the immune system, whereas a too high amount will result in unnecessary high costs of the product. In one embodiment, the fucosylated non-digestible human milk oligosaccharide for use according to the present invention consists of fucosyllactose. In one embodiment, the fucosylated non-digestible human milk oligosaccharide for use according to the present invention consists of 2'-fucosyllactose.

Non-Digestible Oligosaccharides Other than Human Milk Oligosaccharides

The nutritional composition preferably comprises non-digestible oligosaccharides other than HMO. Preferably the NDO other than HMO stimulates the growth of bifidobacteria and/or lactobacilli, more preferably bifidobacteria. An increased content of bifidobacteria and/or lactobacilli stimulate the formation of a healthy intestinal microbiota. The NDO are preferably not or only partially digested in the intestine by the action of acids or digestive enzymes present in the human upper digestive tract, in particular in the small intestine and stomach, and are fermented by the human intestinal microbiota. For example, sucrose, lactose, maltose and the common maltodextrins are considered digestible.

Preferably the present composition comprises non-digestible oligosaccharides with a DP in the range of 2 to 250, more preferably 2 to 60. The non-digestible oligosaccharide is preferably at least one, more preferably at least two, preferably at least three selected from the group consisting of fructo-oligosaccharides, galacto-oligosaccharides, xylo-oligosaccharides, arabino-oligosaccharides, arabinogalacto-oligosaccharides, gluco-oligosaccharides, chito-oligosaccharides, glucomanno-oligosaccharides, galactomanno-oligosaccharides and mannan-oligosaccharides. The group of fructo-oligosaccharides includes inulins and the group of galacto-oligosaccharides includes transgalacto-oligosaccharides or beta-galacto-oligosaccharides.

More preferably the present composition comprises fructo-oligosaccharides (FOS), galacto-oligosaccharides (GOS) and/or beta-galacto-oligosaccharides. More preferably the fructo-oligosaccharides are long chain fructo-oligosaccharides (lcFOS). More preferably the galacto-oligosaccharides are short chain galacto-oligosaccharides and the beta-galacto-oligosaccharides are short chain beta-galacto-oligosaccharides. Most preferably the composition comprises long chain fructo oligosaccharides and short chain galacto-oligosaccharides.

The galacto-oligosaccharides preferably are beta-galacto-oligosaccharides. In a particularly preferred embodiment the present composition comprises beta-galacto-oligosaccharides ([galactose]n-glucose; wherein n is an integer ranging from 2 to 60, i.e. 2, 3, 4, 5, 6, . . . , 59,60; preferably n is selected from 2, 3, 4, 5, 6, 7, 8, 9, and 10), wherein the galactose units are in majority linked together via a beta linkage. Beta-galacto-oligosaccharides are also referred to as trans-galacto-oligosaccharides (TOS). Beta-galacto-oligosaccharides are for example sold under the trademark Vivinal™ (Borculo Domo Ingredients, Netherlands). Another suitable source is Bi2Munno (Clasado). Preferably the TOS comprises at least 80% beta-1,4 and beta-1,6 linkages based on total linkages, more preferably at least 90%.

Fructo-oligosaccharide is a NDO comprising a chain of beta-linked fructose units with a DP or average DP of 2 to 250, more preferably 2 to 100, even more preferably 10 to 60. Fructo-oligosaccharide includes inulin, levan and/or a mixed type of polyfructan. An especially preferred fructo-oligosaccharide is inulin. Fructo-oligosaccharide suitable for use in the compositions is also commercially available, e.g. Raftiline®HP (Orafti). Preferably the fructo-oligosaccharide has an average DP above 20.

In a preferred embodiment the composition comprises a mixture of inulin and short chain fructo-oligosaccharides. In a preferred embodiment the composition comprises a mixture of galacto-oligosaccharides and fructo-oligosaccharides selected from the group consisting of short chain fructo-oligosaccharides and inulin, more preferably inulin. A mixture of at least two different non-digestible oligosaccharides advantageously stimulates the beneficial bacteria of the intestinal microbiota to a greater extent. Preferably the weight ratio in a mixture of the two different non-digestible oligosaccharides, preferably galacto-oligosaccharides and fructo-oligosaccharide, is between 25 and 0.05, more preferably between 20 and 1. Galacto-oligosaccharides, preferably beta-galacto-oligosaccharides, are more capable of stimulating bifidobacteria. Preferably the present composition comprises galacto-oligosaccharides, preferably beta-galacto-oligosaccharides, with a degree of polymerization (DP) of 2 to 10 and/or fructo-oligosaccharides with a DP of 2 to 60.

In a preferred embodiment the composition does not comprise non-digestible acid oligosaccharides other than HMO. In particular, in a preferred embodiment the composition does not comprise non-digestible acid oligosaccharides that are derived from pectin. Such non-digestible acid oligosaccharides are characterized by the presence of uronic acid containing residues. Thus, in a preferred embodiment the composition does not comprise non-digestible uronic acid oligosaccharides, preferably the composition does not comprise non-digestible uronic acid oligosaccharides with a degree of polymerization of 2 to 250. The term non-digestible uronic acid oligosaccharide as used herein refers to a non-digestible oligosaccharide wherein at least 50% of the residues are selected from the group consisting of guluronic acid, mannuronic acid, galacturonic acid and glucuronic acid.

Compositions

The present invention advantageously concerns a composition wherein the lipid provides 5 to 50% of the total calories, the protein provides 5 to 50% of the total calories, and the carbohydrate provides 15 to 90% of the total calories. Preferably, in the present composition the lipid provides 35 to 50% of the total calories, the protein provides 7.5 to 12.5% of the total calories, and the carbohydrate provides 40 to 55% of the total calories. For calculation of the % of total calories for the protein component, the total of energy provided by the proteins, peptides and amino acids needs to be taken into account.

The present composition preferably comprises at least one lipid selected from the group consisting of animal lipid (excluding human lipids) and vegetable lipids. Preferably the present composition comprises a combination of vegetable lipids and at least one oil selected from the group consisting of fish oil, animal oil, algae oil, fungal oil, and bacterial oil. The present composition comprising non-digestible oligosaccharides and *B. breve* excludes human milk.

The present composition preferably comprises protein. The protein component used in the nutritional preparation are preferably selected from the group consisting of non-human animal proteins (preferably milk proteins, preferably proteins from cow's milk), vegetable proteins (preferably soy protein and/or rice protein), free amino acids and mixtures thereof. The present composition preferably contains casein, whey, hydrolysed casein and/or hydrolysed whey protein. Preferably the protein comprises intact proteins, more preferably intact bovine whey proteins and/or intact bovine casein proteins.

The present composition preferably comprises digestible carbohydrates. The present composition preferably comprises a digestible carbohydrate component, wherein at least 35 wt. %, more preferably at least 50 wt. %, more preferably at least 75 wt. %, even more preferably at least 90 wt. %, most preferably at least 95 wt. % is lactose. The present composition preferably comprises at least 25 grams lactose per 100 gram dry weight of the present composition, preferably at least 40 grams lactose/100 gram.

The liquid nutritional composition preferably has a caloric density between 0.1 and 2.5 kcal/ml, even more preferably a caloric density of between 0.5 and 1.5 kcal/ml, most preferably between 0.6 and 0.8 kcal/ml. The amount of nutritional composition administered per day is preferably between 50 and 2000 ml, more preferably between 200 and 1500, most preferably between 400 and 1000 ml.

In a preferred embodiment the preterm formula comprises from 5 to 25 wt. % protein, preferably 9 to 20 wt. %, more preferably 13 to 18 wt. % protein based on the dry weight of the preterm formula. In a preferred embodiment the preterm formula comprises from 1.8 to 3.0 g protein, preferably, preferably 2.0 to 3.0 g, preferably 2.5 g to 2.6 g protein, per 100 ml.

In one embodiment the present invention concerns a supplement, suitable to fortify human milk, to fortify human milk fortified with a standard human milk fortifier or to fortify a standard preterm formula. In the context of this invention, a supplement does not comprise all macro- and micronutrients needed for preterm infants so as to achieve a growth similar to fetal growth coupled with satisfactory functional development.

Thus in one embodiment the nutritional composition according to the present invention or for use according to the present invention comprises protein, fat and/or digestible carbohydrates and is selected from the group consisting of an infant starter formula, an infant follow on formula, a toddler milk, a preterm formula, a post discharge formula and a human milk fortifier.

Application

The present method or use is specifically intended for infants and/or toddlers. Infants have an age of 0-12 months, toddlers have an age of 12-36 months.

The present composition is preferably enterally administered, more preferably orally. The present composition is preferably a nutritional formula, preferably an infant formula. The present composition can advantageously be applied as a complete nutrition for infants. The present composition preferably comprises lipid, protein, and carbohydrate and is preferably administered in liquid form. The present invention includes dry compositions, e.g. powders, which are accompanied with instructions as to admix said dry compositions, in particular nutritional formula, with a suitable liquid, e.g. water.

In one embodiment, the present invention of enhancing vaccine specific immune response in a male human subject comprises administering the non-digestible human milk oligosaccharide according to the invention, or a composition comprising the non-digestible human milk oligosaccharide according to the invention, to the male human subject. Preferably the male human subject is a male infant and the composition is administered via an infant formula. Benefits of this mode of administration include minimizing additional handlings for the caretaker, certainty about the administered dose as well as certainty of administration.

In one embodiment, the composition is administered via the mother during pregnancy and/or breast feeding. This comprises supplementing the diet of the mother with a fucosylated non-digestible human milk oligosaccharide, or a composition comprising a fucosylated non-digestible human milk oligosaccharide, preferably supplementing the diet of the mother with a fucosylated non-digestible human milk oligosaccharide combined with galacto-oligosaccharide and/or fructo-oligosaccharide, more preferably combined with galacto-oligosaccharide and fructo-oligosaccharide. The benefit of administering the present composition via the mother during pregnancy and/or breast feeding is that this enhances the vaccination response at the earliest age possible. After breast feedings has stopped, the composition is preferably administered via the infant formula as this ensures continuous administration of the composition and an optimally enhanced vaccination response.

In one embodiment the administration of the composition according to the invention starts prior to vaccination. Hence, preferably the composition according to the invention is administered during pregnancy and/or infancy, which is from 0-12 months, and/or toddlerhood, which is from 12-36 months, and the enhanced vaccine specific immune response is later-in-life, preferably in adulthood.

Vaccination is a method for protection against specific diseases. Usually the method of vaccination involves administering a composition called a vaccine comprising an antigen to a subject which results in a boost of the immune system. There are multiple types of vaccines. Firstly there is the inactivated vaccine which (largely) comprises dead pathogens. Secondly there is the attenuated vaccine which comprises weakened pathogens. Then there are virus-like particles that resemble viruses but are much less pathogenic. And finally there is the subunit vaccine which comprises the antigen but not the viral particles. In one embodiment, the present invention of enhancing vaccine specific immune response is a vaccine response following vaccination with inactivated vaccine. In one embodiment, the present invention of enhancing vaccine specific immune response is a vaccine response following a single vaccination, preferably following a single vaccination with inactivated vaccine.

The enhanced vaccine specific immune response is preferably an enhanced antibody response, most preferably an enhanced IgG response.

The effectiveness of vaccination depends on a large number of variables, which can be split-up in vaccine-related vaccination effects and subject-related vaccination effects.

The vaccine-related vaccination effects comprise the effectiveness of the particular vaccine, its concentration and how often it is administered.

The subject-related vaccination effects include the subjects general health but also its susceptibility for vaccination. The subject's general health effect resides not only in that healthy humans are less likely to become ill, but also in that they have better chances of a quick recover. These effects are closely related to the subjects overall immune fitness. This concept of immune fitness refers to the health of the immune system or the ability of the immune system to neutralize a harmful pathogen. An immune system that is fit has the ability to respond quickly and adequately to a potentially harmful pathogen. Hence in one embodiment the present invention is for improving immune fitness in a male human subject by administering the non-digestible human milk oligosaccharide according to the invention, or a composition comprising the non-digestible human milk oligosaccharide according to the invention to the male human subject.

A closely related concept is the immune balance. The immune system needs to be respond adequately and quickly to any protruding pathogen. When the immune system reacts too late or when the reaction is not adequate, the immune system is said to be underactive. Subjects with an underactive immune system have an increased susceptibility to infections and diseases. On the other hand when the immune system can be overactive. This also leads to physical complaints such as autoimmune diseases or allergies. A good example of an overactive immune system is pollen allergy where harmless pollen are mistakenly seen as pathogens. The immune system mistakenly reacts to the harmless pollen causing all sorts of complaints. A healthy immune system is neither overactive nor underactive. Instead it is balanced between these two extremes. Hence a healthy immune system necessarily is a balanced immune system.

Hence in one embodiment the present invention is for restoration of immune balance in a male human subject by administering the non-digestible human milk oligosaccharide according to the invention, or a composition comprising the non-digestible human milk oligosaccharide according to the invention to the male human subject.

A widely-used vaccine is the influenza vaccine, which helps protecting against the influenza virus. Influenza vaccines are available in different forms. There are, for instance, the trivalent or quadrivalent injections which contain the inactivated form of the virus. Also there is the nasal spray which comprises the attenuated form of the virus. In a preferred embodiment, the enhanced influenza vaccination response in males of the invention is an enhanced influenza vaccination response to a vaccination with inactivated virus.

In a preferred embodiment, the enhanced influenza vaccination response in males of the invention is an enhanced influenza vaccination response to a single vaccination, preferably a single trivalent influenza vaccination. In a preferred embodiment, the enhanced influenza vaccination response in males of the invention is an enhanced influenza vaccination response to a single vaccination with inactivated virus, preferably a single trivalent influenza vaccination of inactivated virus particles.

As the influenza virus rapidly changes, new vaccines are produced often. This is usually done in fertilized chicken eggs. To produce the trivalent vaccine, three strains (H1N1, H3N2, and a B-strain) are isolated and subsequently used to make the vaccine.

EXAMPLES

Example 1: Immune Response of Male and Female Mice on a Prebiotic Diet

Materials and Methods

BALB/c breeding pairs were fed either control diet (AIN93G) from the day of timed mating or a prebiotic diet containing short-chain galacto-oligosaccharides, long-chain fructo-oligosaccharides and the human milk specific oligosaccharide 2'-FL (scGOS at 0.9 wt. %/lcFOS at 0.1 wt. %/2'-FL at 1 wt. % (total of 2 wt. %)). The AIN93G diet in the control group was adjusted with cellulose fibre to provide comparable diets and fully compensated for the presence of carrier material used to introduce the Vivinal® GOS syrup (scGOS), Inulin HP® (lcFOS fibre) and 2'-FL. ⅓ rd of the litters from the control breeding pairs were switched to prebiotic diet within 24 hours after birth or at weaning and maintained on this throughout the course of the experiment. At 6 weeks of age male and female offspring of all 4 dietary groups were immunized subcutaneously in the scruff of the neck with 1:5 of the human adult dose of trivalent influenza vaccine (TIV, Fluvax 2015) per mouse (100 µl vaccine+100 µl PBS). Mice were tail bled at days 0, 28 and 49, serum was stored at −20° C. until analysis for TIV-specific antibodies by ELISA. Optical density measurements were used to quantify the ELISA colour change.

Results

Only in males receiving the diet comprising 2'-FL, a significant higher concentration of IgG2a, a statistically significant ($p<0.01$) higher concentration of IgG1 and a statistically significant ($p<0.05$) higher concentration of total IgG compared to the control group was found. This finding shows that the males have a significant increase in vaccine specific antibody response due to this fucosylated HMO, hence have an enhanced vaccine specific immune response. This result is indicative for an improved immune fitness and/or restoration of immune balance.

Example 2: Infant Formula for Improving Immune Fitness, Restoration of Immune Balance and/or Enhancing Vaccine Specific Immune Response An infant formula according to the invention comprising per 100 ml (13.9 dry weight):
1.4 g protein (whey and casein)
7.3 g digestible carbohydrates (including lactose)
3.6 g fat (vegetable fat, fish oil)
0.6 g non-digestible oligosaccharides of which 60 mg 2'-fucosyllactose and 480 mg beta-galacto-oligosaccharides, and 60 mg fructo-oligosaccharides Further are included: choline, myo-inositol, taurine, minerals, trace elements, and vitamins in accordance with guidelines.

What is claimed is:

1. A method of enhancing vaccine specific immune response in a male human infant, comprising administering to the infant:
   non-digestible human milk oligosaccharide 2'-fucosyllactose, wherein the composition further comprises short chain galactooligosaccharide and long chain fructo-oligosaccharide followed by administration of only one single vaccination with inactivated vaccine, wherein the vaccine specific immune response is enhanced after the single vaccination and wherein the vaccine specific immune response is a trivalent influenza vaccine response and wherein the administration of the composition starts prior to vaccination.

2. The method according to claim 1, wherein the composition does not comprise non-digestible uronic acid oligosaccharides.

* * * * *